(12) United States Patent
Ostapoff et al.

(10) Patent No.: US 8,529,819 B2
(45) Date of Patent: Sep. 10, 2013

(54) WOUND CLOSURE MATERIAL

(75) Inventors: Roland Ostapoff, East Haven, CT (US); Brian Nentwick, Greenfield Center, NY (US); Richard Stevenson, Colchester, CT (US)

(73) Assignee: Covidien LP, Mansfield, MA (US)

( * ) Notice: Subject to any disclaimer, the term of this patent is extended or adjusted under 35 U.S.C. 154(b) by 940 days.

(21) Appl. No.: 12/527,449

(22) PCT Filed: Mar. 5, 2008

(86) PCT No.: PCT/US2008/002978
§ 371 (c)(1),
(2), (4) Date: Nov. 10, 2009

(87) PCT Pub. No.: WO2008/109123
PCT Pub. Date: Sep. 12, 2008

(65) Prior Publication Data
US 2010/0059570 A1    Mar. 11, 2010

Related U.S. Application Data

(60) Provisional application No. 60/905,532, filed on Mar. 6, 2007.

(51) Int. Cl.
*B27N 3/18* (2006.01)
*B28B 3/00* (2006.01)
*B28B 3/02* (2006.01)
*B29C 41/46* (2006.01)
*B29C 43/02* (2006.01)
*B29C 43/32* (2006.01)
*B29C 51/00* (2006.01)

(52) U.S. Cl.
USPC ......... 264/319; 264/175; 264/500; 264/210.1

(58) Field of Classification Search
USPC .............................. 264/175, 319, 500, 210.1
See application file for complete search history.

(56) References Cited

U.S. PATENT DOCUMENTS

| | | | |
|---|---|---|---|
| 3,490,675 A | 1/1970 | Green et al. | |
| 4,300,565 A | 11/1981 | Rosensaft et al. | |
| 4,681,588 A | 7/1987 | Ketharanathan | |
| 4,781,183 A | 11/1988 | Casey et al. | |
| 4,983,180 A | 1/1991 | Kawai et al. | |
| 5,040,715 A | 8/1991 | Green et al. | |
| 5,110,852 A | 5/1992 | Gogolewski et al. | |
| 5,307,976 A | 5/1994 | Olson et al. | |
| 5,312,023 A | 5/1994 | Green et al. | |
| 5,318,221 A | 6/1994 | Green et al. | |
| 5,326,013 A | 7/1994 | Green et al. | |
| 5,332,142 A | 7/1994 | Robinson et al. | |
| 5,455,110 A | 10/1995 | Connor | |
| 5,468,253 A * | 11/1995 | Bezwada et al. | 606/230 |
| 5,707,385 A | 1/1998 | Williams | |
| 5,759,569 A | 6/1998 | Hird et al. | |
| 5,810,855 A | 9/1998 | Rayburn et al. | |
| 5,915,616 A | 6/1999 | Viola et al. | |
| 5,947,893 A | 9/1999 | Agrawal et al. | |
| 5,964,394 A | 10/1999 | Robertson | |
| 6,241,139 B1 | 6/2001 | Milliman et al. | |
| 6,273,897 B1 | 8/2001 | Dalessandro et al. | |
| 6,330,965 B1 | 12/2001 | Milliman et al. | |
| 6,355,699 B1 | 3/2002 | Vyakarnam et al. | |
| 6,506,873 B1 | 1/2003 | Ryan | |
| 2003/0120284 A1 | 6/2003 | Palacios et al. | |
| 2005/0038472 A1 | 2/2005 | Furst | |
| 2005/0208100 A1 | 9/2005 | Weber et al. | |
| 2005/0245965 A1 | 11/2005 | Orban, III et al. | |
| 2006/0085034 A1 | 4/2006 | Bettuchi | |
| 2006/0121117 A1 | 6/2006 | Hunter et al. | |
| 2006/0135992 A1 | 6/2006 | Bettuchi et al. | |
| 2006/0194292 A1 | 8/2006 | Upton et al. | |
| 2009/0226500 A1 | 9/2009 | Avelar et al. | |

FOREIGN PATENT DOCUMENTS

WO    WO 2008/109123 A2    9/2008

OTHER PUBLICATIONS

European Search Report for EP 10250641.7-1219 date of completion is Oct. 2, 2012 (5 pages).
European Search Report for EP 10251720.8-1269 date of completion is Jan. 17, 20114 (3 pages).
International Search Report for PCT/US08/002978 date of completion is Jul. 29, 2008 (2 pages).

* cited by examiner

*Primary Examiner* — Michael C Miggins

(57) ABSTRACT

Articles are provided having no orientation or a multi-directional orientation. Such articles may be in the form of films, ribbons, sheets, and/or tapes and may be utilized as buttresses with a surgical stapling apparatus or as reinforcing means for suture lines.

22 Claims, No Drawings

WOUND CLOSURE MATERIAL

CROSS-REFERENCE TO RELATED APPLICATIONS

This application is a National Stage Application of PCT/US2008/002978 under 35 USC §371 (a), which claims priority of U.S. Provisional Patent Application No. Ser. 60/905,532 filed Mar. 6, 2007, the disclosures of each of the above-identified applications are hereby incorporated by reference in their entirety.

BACKGROUND

1. Technical Field

The present disclosure relates to articles of polymeric materials in tape, ribbon, sheet, and/or film configurations. These polymeric materials may be formed so that they possess no orientation or multi-directional orientation, which may enhance the integrity of the polymeric material when multidirectional forces are applied thereto. The polymeric materials of the present disclosure may be utilized in numerous applications including, in embodiments, as surgical buttresses or reinforcing tapes for staple or suture lines.

2. Background of Related Art

Films, ribbons, sheets, tapes, and the like which are made of polymeric materials are within the purview of those skilled in the art. Such materials may be produced by melting the polymeric material, extruding the material through a die, and then cooling the resulting material. This process may be very similar to methods utilized for forming filaments or films. The resulting material may be subsequently drawn at various draw ratios through a series of draw stations coupled with heated ovens or similar means in various configurations. This process may be coupled or de-coupled. The resulting drawn material, which may be in the form of a film, ribbon, sheet, tape, and the like, is usually highly oriented in a single direction, i.e., it possesses unidirectional orientation, linearly down its length (the direction in which it was drawn).

The straight pull tensile properties of these materials are usually measured in the same direction as their orientation. Such materials may thus possess great strength when pull forces are applied along the length of the material. While this unidirectional orientation may be desirable for certain uses, for example where similar extrusion, spinning and drawing methods are utilized to produce fibers such as sutures, filaments, and the like, such methods to produce tapes, ribbons, sheets, films, and the like may not be as desirable. This may be especially so where forces which are perpendicular to the unidirectional orientation of the material are applied, which may result in punctures, tears, or cuts in the polymeric material. In some cases, these tears may occur with the application of little force, which may be undesirable.

Surgical stapling devices have found widespread application in surgical operations where body tissue is joined or removed. While buttresses may be used in conjunction with stapling devices or sutures to enhance sealing of wounds, materials possessing a unidirectional orientation as described above may crack or tear with the application of small amounts of force. Moreover, when these materials are perforated by a staple or needle, propagating tears may form parallel to the unidirectional orientation, leading to premature material failure when forces are applied perpendicular to the orientation of the polymer.

Thus, it would be advantageous to provide a material for use with existing wound closure methods to enhance the sealing of a wound. Such materials may be utilized in conjunction with a surgical stapling device as well as sutures and other wound closure methods.

SUMMARY

According to an aspect of the present disclosure, a method is provided, including obtaining a polymeric material selected from the group consisting of glycolic acid, lactic acid, glycolide, lactide, dioxanone, trimethylene carbonate, caprolactone, and combinations thereof; forming the polymeric material into an article that does not possess orientation in a single direction; and recovering the article.

In some embodiments, the polymeric material comprises a copolymer including glycolide in amounts from about 60% to about 75% by weight of the copolymer and trimethylene carbonate in amounts from about 25% to about 40% by weight of the copolymer.

In some embodiments, the polymeric material comprises a copolymer including glycolide in amounts from about 55% to about 65% by weight of the copolymer, dioxanone in amounts from about 10% to about 18% by weight of the copolymer, and trimethylene carbonate in amounts from about 17% to about 35% by weight of the copolymer.

In some embodiments, the polymeric material comprises a copolymer including caprolactone in amounts from about 14% to about 20% by weight of the copolymer, lactide in amounts from about 4% to about 10% by weight of the copolymer, trimethylene carbonate in amounts from about 4% to about 10% by weight of the copolymer, and glycolide in amounts from about 60% to about 78% by weight of the copolymer.

In some embodiments, the step of forming the polymeric material into an article comprises forming an article selected from the group consisting of ribbons, tapes, sheets, and films.

In some embodiments, the step of forming the polymeric material into an article that does not possess orientation in a single direction results in an article possessing no orientation.

In some embodiments, the step of forming the polymeric material into an article that does not possess orientation in a single direction results in an article possessing multi-directional orientation.

In some embodiments, the step of forming the polymeric material into an article that does not possess orientation in a single direction occurs by a process selected from the group consisting of compression rollers, contoured rollers, heat pressing, blown film methods, and combinations thereof.

In some embodiments, the step of forming the polymeric material into an article that does not possess orientation in a single direction occurs by subjecting the polymeric material to a temperature of from about 95° C. to about 230° C. and a pressure of from about 1 psi to about 2500 psi, for a period of time from about 5 seconds to about 10 minutes.

In some embodiments, the step of forming the polymeric material into an article that does not possess orientation in a single direction occurs by introducing the polymeric material into a barrel heated to a temperature of from about 290° F. to about 355° F., extruding the polymeric material through a die having a diameter of from about 1 inch to about 1.5 inches to produce a tubular film, expanding the tubular film to a diameter of from about 2 inches to about 4 inches, and flattening the tubular film to produce a film having a thickness from about 0.001 inches to about 0.014 inches.

In some embodiments, the method further includes forming a texture on at least one surface of the article.

In some embodiments, the article possesses a thickness of from about 0.0005 inches to about 0.014 inches.
}

In some embodiments, the article possesses a thickness of from about 0.002 inches to about 0.005 inches.

In some embodiment, a method is disclosed for producing a surgical staple buttress.

In some embodiment, a method is disclosed for producing a suture line reinforcement strip.

In an embodiment, there is provided a surgical stapling apparatus including a staple cartridge containing at least one staple; an anvil having a staple forming surface; and a buttress positioned adjacent the anvil or the cartridge, the buttress comprising an article produced by a method including obtaining a polymeric material selected from the group consisting of glycolic acid, lactic acid, glycolide, lactide, dioxanone, trimethylene carbonate, caprolactone, and combinations thereof; forming the polymeric material into an article that does not possess orientation in a single direction; and recovering the article.

In an embodiment, there is provided a method of sealing a wound including enclosing tissue between a cartridge and an anvil of a surgical stapling apparatus, one of the cartridge or anvil having a buttress positioned adjacent thereto, wherein the buttress comprises an article produced by a method including obtaining a polymeric material selected from the group consisting of glycolic acid, lactic acid, glycolide, lactide, dioxanone, trimethylene carbonate, caprolactone, and combinations thereof; forming the polymeric material into an article that does not possess orientation in a single direction; and recovering the article; and ejecting staples from the cartridge to secure the buttress to the tissue.

Polymeric articles are provided that do not possess orientation in a single direction, i.e., they may have no orientation or multi-directional orientation. The polymeric articles may be suitable for use in connection with a surgical stapling apparatus or similar wound closure devices to assist in the sealing of tissue to prevent the leakage of fluids and gases.

DETAILED DESCRIPTION

Polymeric articles in the form of tapes, ribbons, sheets, films, and the like are provided in accordance with the present disclosure made of materials that are not highly oriented in a single direction, i.e., they may have no orientation or multi-directional orientation. Where the materials possess multi-directional orientation, the materials may be more oriented in one direction, with some orientation in a different direction, in embodiments a perpendicular direction, or the materials may possess omni-directional orientation, i.e., being oriented in all directions. In embodiments, the polymeric materials may be utilized to form buttresses or similar materials for use in conjunction with wound closure devices such as staplers and sutures to enhance wound closure.

Suitable materials for use in forming the polymeric tapes, ribbons, sheets, and films may include any biocompatible material. Thus, the polymeric articles may be formed from a natural material or a synthetic material. The polymeric article may be bioabsorbable or non-bioabsorbable. It should of course be understood that any combination of natural, synthetic, bioabsorbable and/or non-bioabsorbable materials may be used. Some non-limiting examples of materials which may be used to form articles of the present disclosure include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and combinations thereof.

In embodiments, suitable materials which may be utilized to form the articles of the present disclosure such as tapes, ribbons, sheets, films, and the like, include homopolymers, copolymers, and/or blends possessing glycolic acid, lactic acid, glycolide, lactide, dioxanone, trimethylene carbonate, caprolactone, and various combinations of the foregoing. For example, in some embodiments, a copolymer of glycolide and trimethylene carbonate may be utilized. Methods for forming such copolymers are within the purview of those skilled in the art and include, for example, the methods disclosed in U.S. Pat. No. 4,300,565, the entire disclosure of which is incorporated by reference herein. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments from about 30% to about 35% by weight of the copolymer.

Other suitable materials for forming articles of the present disclosure include, in embodiments, copolymers of glycolide, dioxanone and trimethylene carbonate. Such materials may include, for example, copolymers possessing glycolide in amounts from about 55% to about 65% by weight of the copolymer, in embodiments from about 58% to about 62% by weight of the copolymer, in some embodiments about 60% by weight of the copolymer; dioxanone in amounts from about 10% to about 18% by weight of the copolymer, in embodiments from about 12% to about 16% by weight of the copolymer, in some embodiments about 14% by weight of the copolymer; and trimethylene carbonate in amounts from about 17% to about 35% by weight of the copolymer, in embodiments from about 22% to about 30% by weight of the copolymer, in embodiments about 26% by weight of the copolymer.

In other embodiments, a copolymer of glycolide, lactide, trimethylene carbonate and ε-caprolactone may be utilized to form an article of the present disclosure. Such materials may include, for example, a random copolymer possessing caprolactone in amounts from about 14% to about 20% by weight of the copolymer, in embodiments from about 16% to about 18% by weight of the copolymer, in some embodiments about 17% by weight of the copolymer; lactide in amounts from about 4% to about 10% by weight of the copolymer, in embodiments from about 6% to about 8% by weight of the copolymer, in some embodiments about 7% by weight of the copolymer; trimethylene carbonate in amounts from about 4% to about 10% by weight of the copolymer, in embodiments from about 6% to about 8% by weight of the copolymer, in embodiments about 7% by weight of the copolymer; and glycolide in amounts from about 60% to about 78% by weight of the copolymer, in embodiments from about 66% to about 72% by weight of the copolymer, in embodiments about 69% by weight of the copolymer.

Methods for forming such copolymers are within the purview of those skilled in the art. In embodiments, the individual monomers may be combined in the presence of an initiator, such as diethylene glycol, and a catalyst, such as stannous octoate. The materials may be combined for a suitable period of time from about 4 hours to about 8 hours, in embodiments from about 5 hours to about 7 hours, in other embodiments for about 6 hours. In some cases the mixture may be held under an inert atmosphere, such as under nitrogen gas. The mixture may then heated to a temperature from about 80° C. to about 120° C., in embodiments from about 90° C. to about 110° C., in some cases to about 100° C., for a suitable period of time of from about 5 minutes to about 30 minutes, in embodiments from about 10 minutes to about 20 minutes, in other embodiments for about 15 minutes. The reaction mixture may then be heated to a temperature from about 130° C. to about 170° C., in embodiments from about 140° C. to about 160° C., in embodiments to about 150° C., for a suitable period of time of from about 5 minutes to about 30 minutes, in embodiments from about 10 minutes to about 20 minutes, in other embodiments for about 15 minutes. The mixture may then be heated to a temperature of from about 170° C. to about 190° C., in embodiments to about 180° C., and allowed to polymerize for a period of from about 14 to about 24 hours, in embodiments from about 16 to about 20 hours, in some embodiments about 18 hours.

Once the polymeric material has been obtained, methods for forming articles such as ribbons, tapes, sheets, and/or films from these materials include, but are not limited to the use of compression rollers, the use of contoured rollers, heat pressing, blown film methods, combinations thereof, and the like.

In a compression roller system, the polymer is melted and extruded from a die of a suitable thickness. As the polymer melt exits the extruder die it may be fed through two rollers opposite each other which press against each other and any film passing there between with sufficient pressure to compress the material to the desired thickness. The rollers can both be cooled, both heated, or have one cooled and one heated. Any method within the purview of those skilled in the art may be utilized to heat and/or cool the rollers. Such methods include, for example, induction, jacketed, air heated, air cooled, contained in an oven or refrigerator, and the like. To reduce unidirectional orientation within the polymer melt, the compressing rollers may rotate at about the same or close to the same speed as collection rollers used to advance the material through the system and match the rate of extrusion of material exiting the die. After passing through a compression roller system, the resulting article may be in a tape, ribbon, sheet, film, or similar configuration.

In other embodiments, contoured rollers may be utilized instead of compression rollers to form the articles of the present disclosure. Current draw station rollers may be cylindrical and draw spun-drawn polymeric material exiting an extruder in one direction leading to the unidirectional orientation of the resulting film. The use of laterally oriented non-cylindrical (e.g., spherical, football-shaped, elliptical) rollers between the draw stations may stretch the film laterally as it moves through the drawing process, thus resulting in both longitudinal and latitudinal orientation of the resulting film. The multidirectional stretching and resulting multidirectional orientation may minimize or avoid the formation .of fracture planes in the resulting material.

In yet other embodiments, articles of the present disclosure, including films, may be formed utilizing a heat press, sometimes referred to herein as a heated hydraulic press. Suitable heat presses are commercially available and include, for example Model #HPB-10 press from Greenerd Press and Machine Co., Inc. (Nashua, N.H.). The polymeric materials may be in any form, including pellets, pre-formed sheets, and the like, when they are placed in the press. The press may be heated to a temperature from about 95° C. to about 230° C., in embodiments from about 130° C. to about 225° C. Where the polymeric material is in pellet form, the pellets may be allowed to melt and spread across the plates of the press. A suitable pressure may be applied to the polymer melt to form an article in accordance with the present disclosure having a desired thickness. Suitable pressures may be from about 1 pounds per square inch (psi) to about 2500 psi, in embodiments from about 10 psi to about 100 psi. The polymeric material may be subjected to this heat and temperature for a sufficient time to form an article of the present disclosure, in embodiments from about 5 seconds to about 10 minutes, in other embodiments from about 15 seconds to about 3 minutes. Articles formed from pellets of a polymeric material utilizing a heat press as described herein may possess multi-directional orientation, thus eliminating fracture planes in the films thus formed.

In other embodiments, a heat press may be utilized to form a film from a pre-formed sheet. For example, the polymer may be extruded from a general purpose extruder through a slit dye. The thickness of the slit may vary from about 0.1 millimeters to about 25.4 millimeters, in some embodiments about 0.5 millimeters. The resulting tape-like material may be too thick for certain applications, including for use as a buttress material in conjunction with a surgical stapler or a support material for a suture line. The resulting tape may thus be placed on the plates of a heated hydraulic press as described above and heated to temperatures from about 95° C. to about 230° C., in embodiments from about 108° C. to about 115° C. Pressure may then be applied from about 25 psi to about 2000 psi, in embodiments from about 50 psi to about 100 psi. Extruded sheets may, in embodiments, possess less crystallinity than films formed from pellets, so less heat and pressure may be necessary to form suitable films therefrom.

In some embodiments, shims or similar spacer devices may be placed on the plates of a heat press to ensure the resulting article, such as a film, possesses a desired thickness. In addition, it may be desirable to utilize a die in the heat press having the general configuration of the desired final product, for example as a staple buttress or suture reinforcing line. After the polymer has been treated in the heat press, the resulting article may possess the configuration of the desired final product and thus require very little additional processing, if any.

In yet other embodiments, a blown film process may be utilized to form an article of the present disclosure. The polymer may be introduced into an extruder which contains a screw/barrel configuration and a jacket fitted with external heating elements to aid in melting the polymer. As would be readily appreciated by one skilled in the art, the temperatures to which the barrel may be heated may vary depending upon the polymer utilized. In embodiments, the barrel may be heated to temperatures of from about 150° C. to about 270° C., in embodiments from about 185° C. to about 250° C. In other embodiments, different areas or sections of the barrel may be heated to different temperatures.

The polymer may be melted and transferred by the screw to the die from which it is extruded through a circular slit to form a tubular film having an initial diameter $D_1$. The tubular film may be expanded by compressed air or a compressed gas such as nitrogen, which enters the system through a die inlet port into the interior of the tubular film and has the effect of blowing up the diameter of the tubular film to a diameter $D_2$. In some embodiments, $D_1$ may be from about 1 inch to about 2 inches, in some embodiments from about 1.25 inches to about 1.75 inches, and $D_2$ may be from about 2 inches to about 6 inches, in some embodiments from about 3 inches to about 5 inches. Means such as air rings may also be provided for directing air about the exterior of the extruded tubular film so as to provide quick and effective cooling and stabilization of the tube. In some embodiments a heated or cooling mandrel or similar device may be used to heat/cool the tubular film, which may be used to control crystallization rates. After a short distance, during which the film is allowed to completely cool and harden, it is collapsed by means of a driven nip roller system, which flattens the material into a sheet of double-thickness film which can, in embodiments, be separated into two sheets of film. The sheets of film can then be cut or similarly treated to form a film possessing desired dimensions. Films of varying thicknesses may be produced, including those having a thickness from about 0.001 inches to about 0.014 inches, in embodiments from about 0.002 inches to about 0.005 inches.

In embodiments, the resulting film may be annealed under a gas such as nitrogen for a period of time of from about 12 hours to about 24 hours, in embodiments from about 14 hours to about 22 hours, in embodiments about 18 hours, at temperatures of from about 40±5° C. at the beginning of the annealing process to about 125±5° C. for about the last six hours of the annealing process, to provide the film, which may be suitable for use as a buttress. After the above annealing treatment, the film may be cooled to room temperature, in embodiments about 21±5° C., for a suitable period of time of from about 1 hour to about 10 hours, in embodiments from about 2 hours to about 8 hours. The above heating and cooling may be varied depending upon the polymer utilized. For example, the above annealing treatment may be suitable, in embodiments, for films made of copolymers including copolymers of glycolide, dioxanone, and trimethylene carbonate, as well as copolymers including copolymers of glycolic acid and trimethylene carbonate.

Other materials, however, may be subjected to other treatments. For example, films including copolymers of glycolide, caprolactone, trimethylene carbonate, and lactide may be annealed by heating at temperatures of from about 40±5° C. to about 90±5° C. for periods of time of from about 9 hours to about 12 hours, in embodiments from about 9.25 hours to about 11 hours, with temperatures of about 90±5° C. for the last 8 hours of heating. After the above annealing treatment, the film may be cooled to room temperature, in embodiments from about 21±5° C., for a period of time of from about 4 hours to about 8 hours.

In embodiments, it may be desirable to provide an article of the present disclosure with a textured surface. For example, the plates of a heated hydraulic press as described above may possess a texture which, in turn, will provide a textured surface to an article such as a film produced with the heated hydraulic press. In other embodiments a separate material possessing a textured configuration, such as a mesh, may be placed on the surface of a plate and the polymer pressed with the heated hydraulic press, so that the presence of the mesh imparts a textured surface to the resulting article. In other embodiments, the rollers as described above may similarly be textured to impart a textured surface to an article of the present disclosure. Separate embossing rollers, plates, or similar devices may be utilized in some embodiments to provide texture to the surfaces of articles of the present disclosure. Such texture may be applied after an article has already been formed by placing the formed article in a press having a means for adding texture or passing it over rollers possessing such texture. In other embodiments the article may be formed utilizing methods wherein texture is imparted to the article during the formation of the article itself. Thus, for example, a heat press possessing platens with a textured surface may be utilized to produce a tape, ribbon, sheet, or film and provide a textured surface to said article in a single step. The use of a single step to form an article and provide texture to a surface thereof may be desirable in some circumstances.

Articles thus produced with a textured surface may have desirable physical properties including an increase in the coefficient of friction as well as an improvement in the general appearance of the article surface. Suitable texture patterns include, but are not limited to, random orientations of lines or other geometric shapes, words, pictures, logos, trademarks, combinations thereof, and the like.

Films, ribbons, tapes, sheets, buttresses, and the like formed in accordance with the present disclosure may have a thickness from about 0.0005 inches to about 0.014 inches, in embodiments from about 0.002 inches to about 0.005 inches, inclusive of any texture formed thereon.

As noted above, in embodiments, the resulting ribbons, tapes, sheets, and/or films may be utilized as buttress materials for stapling devices utilized in wound closure. Similarly, the resulting ribbons, tapes, sheets, and/or films may be utilized as reinforcements for suture lines, either by being placed over a suture line and affixed thereto utilizing means within the purview of those skilled in the art, including adhesives, or by directly suturing the ribbon, tape, sheet, and/or film to tissue adjacent a wound so the ribbon, tape, sheet, and/or film is held in place over the wound by the suture.

As the articles of the present disclosure are oriented in multiple directions or possess no orientation at all, fracture planes and the directionality of the orientation of an article are either eliminated or reduced. The resulting articles are suitable for numerous uses, including use as a staple line reinforcement or a suture line reinforcement. The multi-directional orientation of these materials will improve the tear resistance of the resulting films, ribbons, sheets, and/or tapes as the materials do not possess potential for forming propagating tears which may be formed with tapes having unidirectional orientation.

For example, the films, ribbons, sheets, and/or tapes of the present disclosure may be used with any suture to reinforce the suture line and enhance the sealing of a wound. Moreover, the films, ribbons, sheets, and/or tapes of the present disclosure may be used as a buttress with any stapler utilized in a surgical procedure. Such staplers include linear staplers, annular or circular staplers including those utilized in anastomosis procedures, and the like. Examples of suitable staplers which may be utilized include, for example, those disclosed in U.S. Pat. No. 3,490,675, and U.S. Patent Application Publication Nos. 2006/0085034, 2006/0135992, and 2005/0245965, the entire disclosures of each of which are incorporated by reference herein.

Other examples of stapling apparatus which may be utilized with buttresses formed of the articles described herein includes laparoscopic staplers (see, e.g., U.S. Pat. Nos. 6,330, 965 and 6,241,139, the entire disclosures of each of which are incorporated by reference herein), alternative stapling apparatus of the transverse anastomosis type for stapling a patient's mesentery (see, e.g., U.S. Pat. No. 5,964,394, the entire disclosure of which is incorporated by reference herein), and end-to-end anastomosis types for performing surgical anastomotic stapling with a circular cartridge and anvil mesentery (see, e.g., U.S. Pat. No. 5,915,616, the entire disclosure of which is incorporated by reference herein). Other examples of endoscopic and/or laparoscopic surgical stapling devices which may be utilized with a buttress formed of an article of the present disclosure are disclosed in, for example, U.S. Pat. No. 5,040,715, (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire disclosures of each of which are incorporated by reference herein. Commercially available staplers which may be utilized with a buttress formed of an article of the present disclosure include, but are not limited to, those available from Tyco Healthcare Group, LP under the name Multifire ENDO GIA™ 30 and Multifire ENDO GIA™ 60 instruments.

Buttresses formed of articles of the present disclosure may also be used in conjunction with instruments that apply two-part fasteners wherein a first part of the two-part fastener is stored in a cartridge or like member and can be fired and properly joined to a second part of the two-part fastener disposed in an anvil or like member. Those skilled in the art having read the present disclosure will readily envision how to adapt the present buttresses for use in connection with such apparatus and also envision other surgical apparatus with which the buttresses described herein may be used.

At a minimum, a surgical stapling apparatus utilizing a buttress described herein may possess a staple cartridge containing at least one staple, an anvil having a staple forming surface, and a buttress of the present disclosure positioned adjacent the anvil or the cartridge. Methods for closing a wound with such an apparatus are within the purview of those skilled in the art and may include, in embodiments, first enclosing tissue between the cartridge and anvil of the surgical stapling apparatus. A buttress of the present disclosure may be positioned adjacent the cartridge, the anvil, or both. Staples may then be ejected from the cartridge to secure the buttress to tissue.

Where utilized with a surgical stapler, it is envisioned that the buttress material may be releasably attached to the cartridge and/or the anvil component of a stapler in any manner capable of retaining the buttress in contact with the cartridge and/or the anvil prior to and during the stapling process, while allowing the buttress to be removed or released from the cartridge and/or the anvil following the penetration of the buttress by a surgical staple or other fastening device. For example, the buttress may be attached to the cartridge and/or the anvil using adhesives, sealants, glues, pins, tacks, tabs, clamps, channels, straps, protrusions and combinations thereof.

In some embodiments, at least one bioactive agent may be combined with the buttress material or suture reinforcing material made with a ribbon, tape, sheet, and/or film of the present disclosure. In these embodiments, the article of the present disclosure can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, fragrance, or sealant. Alternatively a bioactive agent could be any agent which provides a therapeutic or prophylactic effect, a compound that affects or participates in tissue growth, cell growth, cell differentiation, an anti-adhesive compound, a compound that seals or provides adhesive forces, a compound that may be able to invoke a biological action such as an immune response, or could play any other role in one or more biological processes. It is envisioned that the bioactive agent may be applied to the ribbon, tape, sheet, and/or film of the present disclosure in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the articles of the present disclosure and the surrounding tissues opposite the target tissue. In addition, anti-adhesive agents may be used to prevent adhesions from forming between the articles of the present disclosure and any packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent with an article of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent with an article of the present disclosure.

Other bioactive agents which may be included as a bioactive agent with an article of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-mitotics; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; telomerase inhibitors; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; antiproliferatives; anti-angiogenic drugs; polymer drugs; bioactive functionalized polymers including polymers possessing phosphoryl cholines and/or furanones; anticonvulsants; antidepressants; antihistamines; and immunological agents.

Other examples of suitable bioactive agents which may be included with an article of the present disclosure include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM- CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; biologic complexes; metal ion complexes; polynucleotides; and ribozymes.

As noted above, in embodiments combinations of any of the foregoing bioactive agents may be added to a film of the present disclosure.

Other bioactive agents which may be included with an article of the present disclosure include chemotherapeutic agents which may, in turn, include radiotherapeutic agents. Any such chemotherapeutic agent and/or radiotherapeutic agent may be included in an article of the present disclosure. Examples of such chemotherapeutic agents include, but are not limited to, radioactive isotopes such as iodine 125, palladium 103, iridium 192, cesium 131, gold 198, yttrium 90 and phosphorus 32, combinations thereof, and the like.

In embodiments, radioactive isotypes may be applied to films of the present disclosure as seeds with the films thus being utilized for brachytherapy.

The following Examples are being submitted to illustrate embodiments of the present disclosure. These Examples are intended as illustrative only and are not intended to limit the scope of the present disclosure. Also, parts and percentages are by weight unless otherwise indicated.

EXAMPLE 1

A film was produced from a polymer which included about 60% by weight glycolide, about 14% by weight dioxanone, and about 26% by weight trimethylene carbonate. Polymer pellets were placed in a heated hydraulic press (Carver Laboratory Press, Model 2626). The press was heated to a temperature from about 125° C. to about 165° C. The pellets were placed in the center of Teflon coated steel plates with steel shims to control the thickness of the resulting film. The pellets were allowed to melt and spread across the plates and a pressure of less than about 100 psi was applied to the polymer melt. The entire apparatus was crash cooled by running water through the plates. Films were obtained having a thickness of from about 0.002 inches to about 0.012 inches. The films had a multi-directional orientation.

EXAMPLE 2

A random copolymer possessing about 17% by weight caprolactone, about 7% by weight lactide, about 7% by weight trimethylene carbonate, and about 69% by weight glycolide was utilized to produce a film. The copolymer was extruded from a ¾ inch general purpose extruder through a slit dye. A thick tape was produced. The resulting tape was placed on Teflon coated steel plates in a hydraulic heat press as described above in Example 1, with the appropriate shims to produce a film having a desired thickness. The heat press was heated to a temperature of about 105° C. to about 120° C. and a pressure of less than about 100 psi was applied. Similar to the films produced in Example 1 utilizing pellets, films produced by this method had a thickness of from about 0.002 inches to about 0.012 inches. As the extruded film had less crystalline structure than the pellets of Example 1, a lower temperature could be used to make the polymer flow. The films had a multi-directional orientation.

EXAMPLE 3

A film was produced with the polymer described above in Example 2 using a blown film process. Polymer pellets were introduced into an extruder (Randcastle Extrusion System, Inc., Cedar Grove, N.J.) possessing a screw/barrel configuration and a jacket fitted with external heating elements. The barrel had three zones held at three different temperatures, with zone 1 being closest to the portion of the barrel into which the polymer pellets were introduced, zone 2 being the mid-portion of the barrel, and zone 3 being the end of the barrel from which the polymer was extruded. The length/diameter ratio of the barrel was 24 to 1, with a ¾ inch screw inside the barrel. A die having a diameter of about 1.25 inches was located at the end of the barrel through which the polymer melt was extruded.

The barrel temperature for zone 1 was about 344° F.; for zone 2, from about 347° F. to about 350° F.; for zone 3, about 294° F.; and for the adaptor between the barrel and the die, about 345° F. The rate of spin of the screw was from about 80.5 revolutions per minute (rpm) to about 81.5 rpm, with the temperature at the die of from about 342° F. to about 346° F. The pressure in the barrel was from about 2000 psi to about 2069 psi, with the pressure at the die at from about 2079 psi to about 2196 psi. The temperature of the polymer melt at extrusion was about 297° F.

The tubular film was expanded by compressed air which entered the system through an inlet into the interior of said tubular film. The compressed air was utilized to expand the diameter of the tubular film to a diameter of about 3 inches. An air ring was utilized to direct the air about the exterior of extruded tubular film so as to provide quick and effective cooling. After a short distance, during which the film was allowed to cool and harden, it was wound up on a take-up roll which flattened the material, and then run through a nip roller, to produce films of varying thicknesses. The thicknesses of the films produced were about 0.003 inches, 0.004 inches, 0.006 inches, and 0.008 inches. The films thus produced had a multi-directional orientation.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A method comprising:
    obtaining a polymeric material selected from the group consisting of glycolic acid, lactic acid, glycolide, lactide, dioxanone, trimethylene carbonate, caprolactone, and combinations thereof;
    forming the polymeric material into an article that does not possess orientation in a single direction by subjecting the polymeric material to a temperature of from about 95° C. to about 230° C. and a pressure of from about 1 psi to about 2500 psi, for a period of time from about 5 seconds to about 10 minutes; and
    recovering the article.

2. The method of claim 1, wherein the polymeric material comprises a copolymer including glycolide in amounts from about 60% to about 75% by weight of the copolymer and trimethylene carbonate in amounts from about 25% to about 40% by weight of the copolymer.

3. The method of claim 1, wherein the polymeric material comprises a copolymer including glycolide in amounts from about 55% to about 65% by weight of the copolymer, dioxanone in amounts from about 10% to about 18% by weight of the copolymer, and trimethylene carbonate in amounts from about 17% to about 35% by weight of the copolymer.

4. The method of claim 1, wherein the polymeric material comprises a copolymer including caprolactone in amounts from about 14% to about 20% by weight of the copolymer, lactide in amounts from about 4% to about 10% by weight of the copolymer, trimethylene carbonate in amounts from about 4% to about 10% by weight of the copolymer, and glycolide in amounts from about 60% to about 78% by weight of the copolymer.

5. The method of claim 1, wherein forming the polymeric material into an article comprises forming an article selected from the group consisting of ribbons, tapes, sheets, and films.

6. The method of claim 1, wherein forming the polymeric material into an article that does not possess orientation in a single direction results in an article possessing no orientation.

7. The method of claim 1, wherein forming the polymeric material into an article that does not possess orientation in a single direction results in an article possessing multi-directional orientation.

8. The method of claim 1, further comprising forming a texture on at least one surface of the article.

9. The method of claim 1, wherein the article possesses a thickness of from about 0.0005 inches to about 0.014 inches.

10. The method of claim 1, wherein the article possesses a thickness of from about 0.002 inches to about 0.005 inches.

11. A method of sealing a wound comprising:
enclosing tissue between a cartridge and an anvil of a surgical stapling apparatus, one of the cartridge or anvil having a buttress positioned adjacent thereto, wherein the buttress comprises an article produced by the method of claim 1; and
ejecting staples from said cartridge to secure the buttress to the tissue.

12. A method comprising:
obtaining a polymeric material selected from the group consisting of glycolic acid, lactic acid, glycolide, lactide, dioxanone, trimethylene carbonate, caprolactone, and combinations thereof;
forming the polymeric material into an article that does not possess orientation in a single direction by introducing the polymeric material into a barrel heated to a temperature of from about 290° F. to about 355° F., extruding the polymeric material through a die having a diameter of from about 1 inch to about 1.5 inches to produce a tubular film, expanding the tubular film to a diameter of from about 2 inches to about 4 inches, and flattening the tubular film to produce a film having a thickness from about 0.001 inches to about 0.014 inches; and
recovering the article.

13. The method of claim 12, wherein the polymeric material comprises a copolymer including glycolide in amounts from about 60% to about 75% by weight of the copolymer and trimethylene carbonate in amounts from about 25% to about 40% by weight of the copolymer.

14. The method of claim 12, wherein the polymeric material comprises a copolymer including glycolide in amounts from about 55% to about 65% by weight of the copolymer, dioxanone in amounts from about 10% to about 18% by weight of the copolymer, and trimethylene carbonate in amounts from about 17% to about 35% by weight of the copolymer.

15. The method of claim 12, wherein the polymeric material comprises a copolymer including caprolactone in amounts from about 14% to about 20% by weight of the copolymer, lactide in amounts from about 4% to about 10% by weight of the copolymer, trimethylene carbonate in amounts from about 4% to about 10% by weight of the copolymer, and glycolide in amounts from about 60% to about 78% by weight of the copolymer.

16. The method of claim 12, wherein forming the polymeric material into an article comprises forming an article selected from the group consisting of ribbons, tapes, sheets, and films.

17. The method of claim 12, wherein forming the polymeric material into an article that does not possess orientation in a single direction results in an article possessing no orientation.

18. The method of claim 12, wherein forming the polymeric material into an article that does not possess orientation in a single direction results in an article possessing multi-directional orientation.

19. The method of claim 12, further comprising forming a texture on at least one surface of the article.

20. The method of claim 12, wherein the article possesses a thickness of from about 0.0005 inches to about 0.014 inches.

21. The method of claim 12, wherein the article possesses a thickness of from about 0.002 inches to about 0.005 inches.

22. A method of sealing a wound comprising:
enclosing tissue between a cartridge and an anvil of a surgical stapling apparatus, one of the cartridge or anvil having a buttress positioned adjacent thereto, wherein the buttress comprises an article produced by the method of claim 12; and
ejecting staples from said cartridge to secure the buttress to the tissue.

* * * * *